(12) United States Patent
Zolle et al.

(10) Patent No.: US 7,358,369 B2
(45) Date of Patent: Apr. 15, 2008

(54) RADIOLABELLED PHENYLETHYL IMIDAZOLE CARBOXYLIC ACID ESTER DERIVATIVES

(75) Inventors: Ilse Zolle, Zimmermanngasse 22/8, Vienna (AT) A-1090; Friedrich Hammerschmidt, Vienna (AT)

(73) Assignee: Ilse Zolle, Vienna (AT)

( * ) Notice: Subject to any disclaimer, the term of this patent is extended or adjusted under 35 U.S.C. 154(b) by 0 days.

(21) Appl. No.: 11/582,073

(22) Filed: Oct. 17, 2006

(65) Prior Publication Data

US 2007/0036718 A1 Feb. 15, 2007

Related U.S. Application Data

(63) Continuation of application No. 10/635,294, filed on Aug. 6, 2003, now Pat. No. 7,189,859.

(51) Int. Cl.
*C07D 233/54* (2006.01)
*A61K 31/4164* (2006.01)

(52) U.S. Cl. ............................ 548/334.5; 548/300.1; 548/333.5; 514/396; 514/399; 514/400

(58) Field of Classification Search ............ 548/300.1, 548/333.5, 334.5; 514/396, 399, 400
See application file for complete search history.

(56) References Cited

U.S. PATENT DOCUMENTS

| 4,770,689 A | * | 9/1988 | Van Gestel et al. | 504/253 |
| 4,851,424 A | * | 7/1989 | Allgeier | 514/400 |
| 7,189,859 B2 | * | 3/2007 | Zolle et al. | 548/334.5 |

* cited by examiner

*Primary Examiner*—Golam M. M. Shameem
(74) *Attorney, Agent, or Firm*—Laurence A. Greenberg; Werner H. Stemer; Ralph E. Locher

(57) ABSTRACT

Halogenated carboxylic ester derivatives of phenylethyl imidazole, and their method of preparation are disclosed. Radio-halogenated forms of these compounds are ideally suited for positron-imaging of the adrenal glands, as it is known that these compounds demonstrate a selective and high rate of accumulation in the adrenals. The method of preparing these derivatives proceeds by the conversion of a stable, non-radioactive intermediate having trialkylstannyl leaving groups. These intermediates are efficiently converted to the corresponding halogenated forms by substitution of the trialkylstannyl group with the halogen or radiohalogen.

5 Claims, 5 Drawing Sheets

Figure 1

Figure 3:
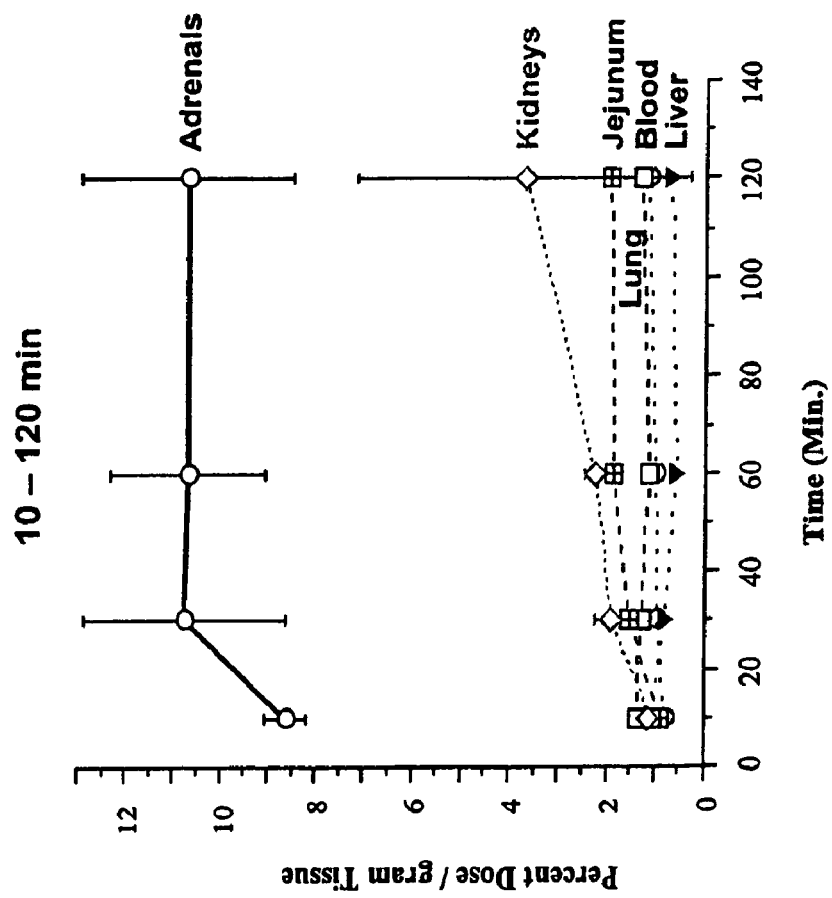

In vitro characterization of the radiotracer [$^{131}$I]MTO

1. [$^{131}$I]MTO binds fast and reversibly to rat adrenal membranes.

2. Saturation analysis suggested a single class of binding sites with an equilibrium constant ($K_D$) = 7.4 ± 2.8 nM 3. All synthetic analogues of MTO were characterized as competitive inhibitors of specific [$^{131}$I]MTO binding to adrenal membranes.

4. Known inhibitors of 11β-hydroxylase acticity (metyrapone, ketoconazole) are also potent displacers of [$^{131}$I]MTO binding.

Figure 2

Inhibition of $^{131}I$-MTO binding by etomidate derivatives

| Inhibitor | $IC_{50}$ (nM) | SD | n |
|---|---|---|---|
| Etomidate | 1.08 | 0.42 | 11 |
| Metomidate | 3.69 | 1.92 | 6 |
| 4-Iodo-metomidate | 9.0 | 3.7 | 15 |
| 2-Fluoro-etomidate | 2.89 | 0.55 | 4 |
| Free acid | 123 µM | 41 | 3 |

Figure 4

Target / Non-Target Ratios obtained with $^{131}$I-MTO

| Organ | 10 | 30 | 60 | 120 (min) |
|---|---|---|---|---|
| Adrenal / Kidney | 7.7 | 5.7 | 4.7 | 2.9 |
| Adrenal / Liver | 8.4 | 13.9 | 19.7 | 15.5 |
| Adrenal / Jejunum | 9.8 | 7.2 | 5.7 | 5.5 |
| Adrenal / Blood | 11.3 | 11.1 | 10.7 | 9.0 |

RADIOLABELLED PHENYLETHYL IMIDAZOLE CARBOXYLIC ACID ESTER DERIVATIVES

SUMMARY OF INVENTION

The invention relates to radioactively labelled derivatives of (R)-3-(1-phenylethyl)-3H-imidazole-4-carboxylic acid esters and methods for preparing these compounds. The invention also relates to the use of these radioactively labelled compounds as radiopharmaceuticals. In particular, these compounds bind selectively to adrenocortical tissue facilitating the diagnosis of adrenal cortical masses such as incidentaloma, adenoma, primary and metastatic cortical carcinoma.

BACKGROUND OF INVENTION

The present invention relates to a class of substituted (R)-3-(1-phenylethyl)-3H-imidazole-4-carboxylic acid esters which interact selectively with the mitochondrial cytochrome P-450 species in the adrenal tissue (Vanden Bossche, 1984). When labelled with radiohalogen (iodine-123; bromine-76; fluorine-18 and otherrs) these compounds serve as radiotracers for the diagnosis of adrenal cortical masses such as incidentalomas, adenomas, primary and metastatic cortical carcinoma. When labelled with a beta-emitting radionuclide (iodine-131; bromine-82), these radiotracers may be used for radionuclide therapy. The main application is for tumour diagnosis (Khan 2003).

In particular, the compounds according to this invention are potent inhibitors of steroid P450$_\beta$hydroxylation and bind with high affinity to adrenocortical membranes. In fact, the compounds in accordance with this invention have been found to possess an almost 1000-fold selective affinity when compared with known, clinically used inhibitors (metyrapone, ketoconazole). Therefore, when injected intravenously, the labelled derivatives of the present invention, accumulate rapidly in the adrenals, reaching radioactivity levels that are diagnostically useful.

The parent compound etomidate (ethyl ester; ETO) is clinically used as a short-acting hypnotic drug. When incubated with human adrenocortical tissue slices, it was shown to block the conversion of 11-deoxycortisol to cortisol and of 11-deoxycorticosterone (DOC) to corticosterone and aldosterone (Weber 1993; Engelhardt 1994). Also metomidate (MTO), the methyl ester, is an equally potent inhibitor of steroid 11β-hydroxylation. (R)-configuration of the methyl substituent at the chiral C-atom is essential for enzyme inhibition (Vanden Bossche, 1984).

Clinical findings with the radiotracer [O-methyl-$^{11}$C]metomidate have indicated high uptake in lesions of adrenocortical origin, including adenomas, but very low uptake in lesions of non-adrenocortical origin (Bergström 1998; 2000). Specific uptake has been reported in multiple metastases in the lung of a primary adrenocortical carcinoma (Mitterhauser 2002). However, the differentiation between benign (e.g., adenoma) and malignant (e.g., carcinoma) is primarily based on the size and shape of the lesion; irregularities in tumour uptake and multiple lesions are an indication of malignancy (Khan 2003).

Although $^{11}$C-metomidate has "ideal" biological characteristics for scintigraphy of the adrenals and tumor derived therefrom, application of the radiopharmaceutical is limited to hospitals with a PET facility. $^{11}$C is a cyclotron product and decays with a half-life of 20 min, therefore, $^{11}$C-metomidate must be synthesized immediately prior to use.

Halogenations, on the other hand, offer sufficient flexibility, time for preparation and shipment. (Iodine-123 $T_{1/2}$=13.2 hours; Br-76 $T_{1/2}$=16 hours).

Enzyme inhibitors, such as metyrapone have been labelled with radioiodine for adrenal scintigraphy, however, these compounds have never been used for clinical diagnosis (Wieland, 1982; Robien & Zolle, 1983). A comparison of the binding affinities ($IC_{50}$-values) of known inhibitors with etomidate clearly demonstrated the higher potency of etomidate and metomidate.

The available radiotracers for imaging the adrenal cortex and adrenal cortex-derived tumors are labelled cholesterol derivatives. These include 6β-[$^{131}$I]-iodomethyl-19-norcholesterol (NP-59) (Basmadjian, 1975) and 6β-[$^{75}$Se]-selenomethyl-19-norcholesterol (Scintadren™) (Sakar, 1976). Both NP-59 and Scintadren™ accumulate in the adrenals slowly, within days, requiring long-lived radionuclides as a label (Iodine-131 $T_{1/2}$=8.04 days; Selen-75 $T_{1/2}$=120 days). Iodine-131 is also emitting beta-radiation, which contritutes considerably to the radiation exposure. The diagnostic use of beta-emitters is no longer state of the art.

In view of the drawbacks of above mentioned agents with respect to patient care (high radiation exposure, repeated imaging procedures), the development of radiolabeled derivatives of etomidate and metomidate would greatly improve radionuclide imaging procedures for the detection and follow-up of adrenal disease.

The invention disclosed herein concerns radiotracers with high selectivity and rapid uptake kinetics, providing metomidate labelled with a SPECT or PET radionuclide with a short physical half-life. $^{123}$I-MTO offers optimal imaging characteristics with SPECT, with high accumulation of the radiotracer in the adrenals, so that imaging may be started 10-15 minutes post injection of the radioactive dose. Radiation exposure to the patient is minimized.

DETAILED DESCRIPTION OF THE DRAWINGS

FIG. 1 summarizes the relevant characteristics of radioiodinated metomidate binding to adrenal membranes.

FIG. 2 provides the $IC_{50}$ of various etomidate derivatives as inhibitors of the binding of radioiodinated metomidate.

FIG. 3 describes the accumulation of radioiodinated metomidate in different organs in vivo, after up to 120 minutes post-injection.

FIG. 4 provides the target:non-target ratios of radioiodinated metomidate after different time intervals post-injection.

Figure 5:
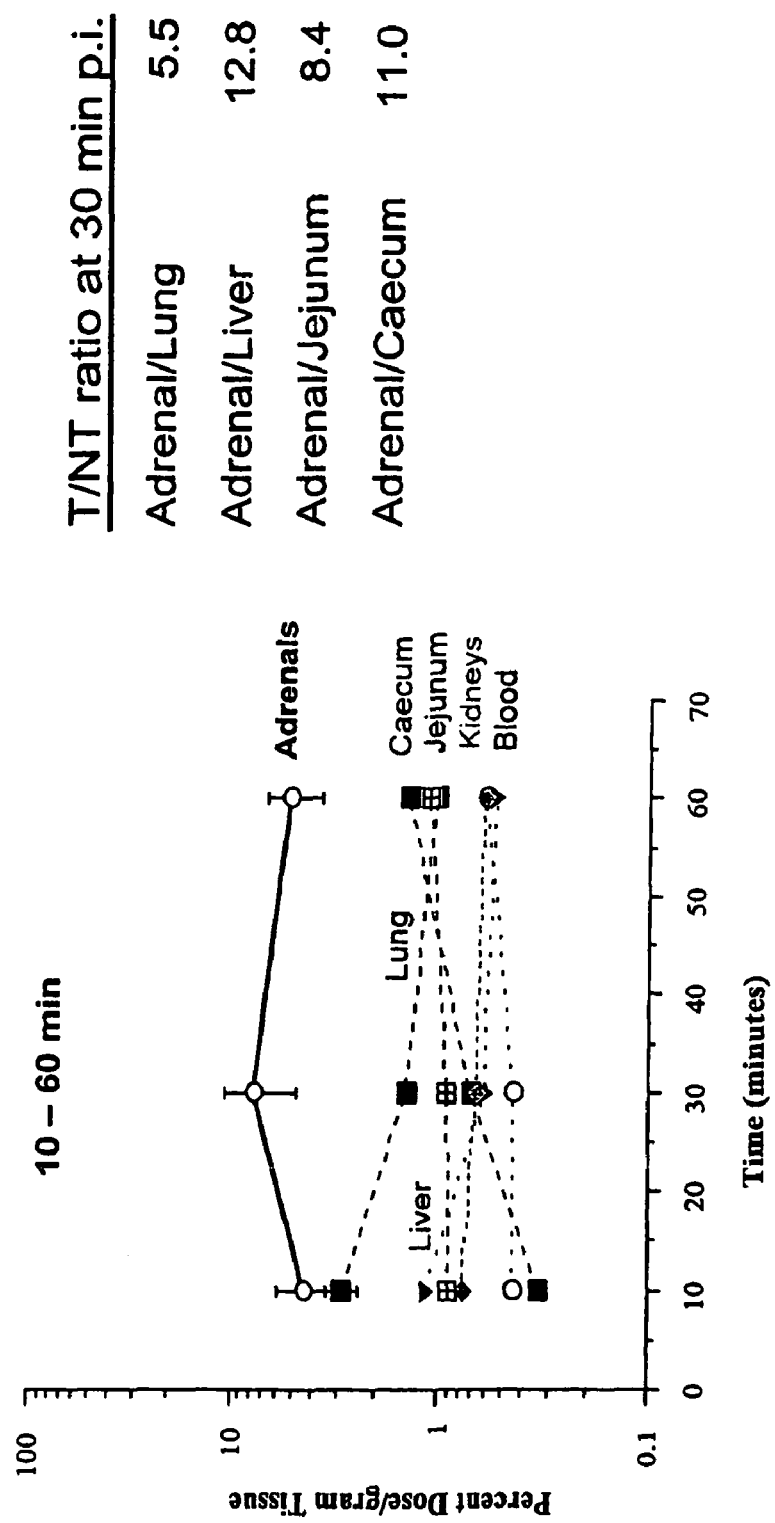

FIG. 5 provides the results of experiments describing the in vivo distribution of radiofluorinated etomidate.

DETAILED DESCRIPTION OF THE INVENTION

The present invention provides a compound of formula I,

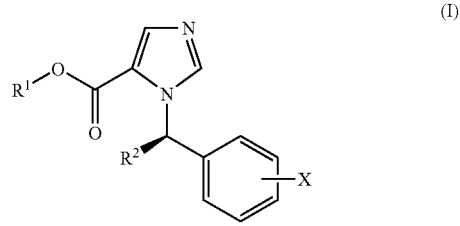

(I)

wherein
- R¹ represents a straight or branched alkyl chain containing from 1 to 4 carbon atoms, wherein the alkyl group is optionally substituted with a halogen;
- R² represents a straight alkyl chain in (R)-configuration containing from 1 to 2 carbon atoms;
- X denotes a halogen or a radiohalogen;

As used herein, the expression "alkyl," includes methyl and ethyl groups, and straight-chained or branched propyl groups. Particular alkyl groups are methyl, ethyl, 2-fluoroethyl, n-propyl, and isopropyl, especially methyl and ethyl.

The term "halogen" as used herein, includes iodine, bromine and fluorine, especially iodine.

The compound of formula (I) in accordance with the present invention is suitably a halogenated derivative of formula IA, and a radiolabelled derivative of formula IB:

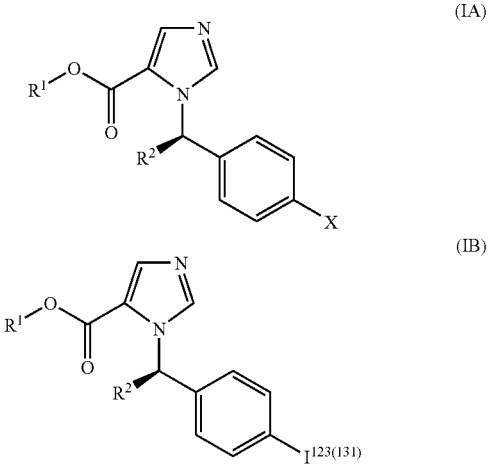

wherein
- R¹ and R² are as defined above;
- X denotes a halogen resp. radioiodine;

Preferred are compounds of formula (IB), wherein R¹ and R² is methyl and X is $^{123}$I or $^{131}$I, namely (R)-3-[1-(4-[$^{123}$I]iodophenyl)ethyl-3H-imidazole-4-carboxylic acid methyl ester ($^{123}$I-MTO) and (R)-3-[1-(4-[$^{131}$I]iodophenyl)ethyl]-3H-imidazole-4-carboxylic acid methyl ester ($^{131}$I-MTO); and wherein R¹ is ethyl, R² is methyl and X is $^{123}$I or $^{131}$I, namely (R)-3-[1-(4-[$^{123}$I]iodophenyl)ethyl-3H-imidazole-4-carboxylic acid acid ethyl ester ($^{123}$I-ETO) and (R)-3-[1-(4-[$^{131}$I]iodophenyl)ethyl]-3H-imidazole-4-carboxylic acid ethyl ester (131I-ETO).

The present invention includes within its scope stannylated derivatives of formula II:

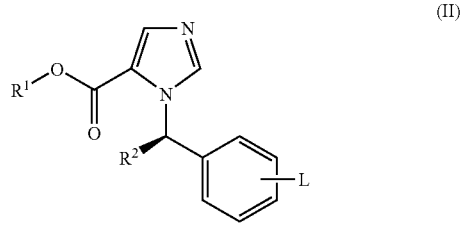

wherein R¹ and R² are as defined above;

L represents a trimethyl-, triethyl-, tri-n-propyl- and a tri-n-butylstannyl group.

The stannylated precursors are prepared from the respective halogenated compounds of formula IA to give IIA:

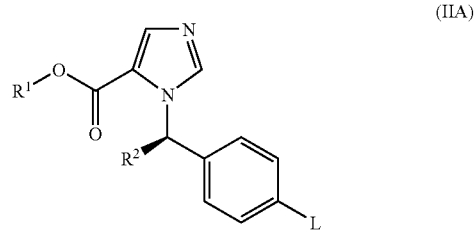

wherein R¹ and R² are as defined above;

L represents a trimethyl-, triethyl-, tri-n-propyl- and a tri-n-butylstannyl group.

Compounds of formula II contain a leaving group L, suitably selected from trimethylstannyl, triethylstannyl, tri-n-propylstannyl and tri-n-butylstannyl, especially trimethylstannyl.

Compounds of formula IIA are key intermediates for radiotracer synthesis by oxidative radiohalogenido destannylation. The trialkylstannyl groups in an aromatic ring can be replaced easily by radiohalogen to yield the respective radioactively labelled compounds of formula (IB).

The invention concerns a process of synthesizing compounds of formula (I) by a stereoselective and regioselective new approach.

The compounds according to the invention may be prepared by a process which comprises coupling a compound of formula III:

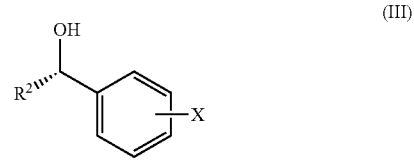

wherein
- R² represents a straight alkyl chain in (S)-configuration containing from 1 to 2 carbon atoms;
- X represents a halogen;
- with a compound of formula IV:

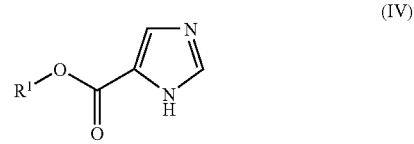

wherein
- R¹ represents a straight or branched alkyl chain containing from 1 to 4 carbon atoms, wherein the alkyl group is optionally substituted with a halogen;

The reaction between compounds III and IV proceeds with inversion of configuration, to give compounds of formula I:

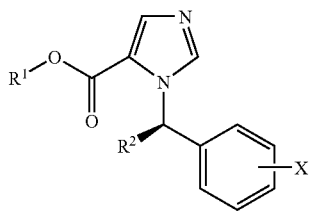

(I)

wherein
- R¹ represents a straight or branched alkyl chain containing from 1 to 4 carbon atoms;
- R² represents a straight alkyl chain in (R)-configuration containing from 1 to 2 carbon atoms;
- X represents a halogen;

Particular alkyl groups are methyl, ethyl, 2-fluoroethyl, n-propyl, and isopropyl, especially methyl and ethyl.

The reaction between compounds III and IV is based on the known Mitsunobu reaction (Mitsunobu, 1981). The alcohol (S)-1-(4-iodophenyl)ethanol (III) is reacted with methyl imidazole-4-carboxylate (IV) in the presence of triphenylphosphane and a dialkyl azodicarboxylate (preferably di-t-butyl azodicarboxylate). Triphenyl phosphinoxide and the hydrazo ester are by-products of the reaction. The reaction conditions favour activation of the alcohol to generate the reactive alkoxyphosphonium salt. Methyl imidazole-4-carboxylate is expected to be deprotonated, thus N-1 and N-3 could react as nucleophile with the alkoxyphosphonium cation to give a mixture of two isomeric N-substituted imidazoles. Yet, when coupling III and IV at low temperature, alkylation is observed exclusively at N-3 with clean inversion.

Previous attempts to react secondary alcohols (alkylaryl or diaryl carbinols) with symmetrical imidazole-4,5-dinitrile produced partial resp. complete racemization by the Mitsunobu reaction (Botta et al., 1994; Corelli et al., 1995).

(S)-III is a key intermediate and needs to be synthesized; methyl imidazole-4-carboxylate IV is commercially available.

Since not commercially available, the starting material of formula III is prepared by a novel synthetic approach, described hereafter and in scheme 1:

Starting from 4-iodophenyl methyl ketone, which is reduced to the racemic alcohol and converted to (±)-1-(4-iodophenyl)ethyl chloroacetate, the racemic ester is subjected to stereoselective enzyme hydrolysis. The remaining (S)-isomer of the ester is separated from the (R)-alcohol and transesterified to give (S)-1-(4-iodophenyl)ethanol (ee >98%) III.

Laumen & Schneider (1988) reported that lipase SAM II hydrolyses acetates and chloroacetates of secondary benzyl alcohols with high enantioselectivity, therefore, Schneider's procedure is applied to the resolution of racemic 1-(4-iodophenyl)ethanol. Lipase SAM II is known to hydrolyse preferentially the (R)-esters of secondary benzyl alcohols; however, application with the substrate described in the invention is new.

(R)-4-Iodo-metomidate is derived exclusively from the (S)-alcohol of the ester which is not accepted as substrate by lipase SAM II. Coupling of (S)-1-(4-iodophenyl)ethanol with methyl imidazole-4-carboxylate yields (R)-4-iodo-metomidate with clean inversion.

This novel reaction offers a versatile approach to the synthesis of compounds described by formula I. (S)-1-(4-iodophenyl)ethanol (ee >98%) III is synthesized by lipase-catalysed resolution and coupled with methyl 4-imidazole carboxylate IV. The two fragments are joined regioselectively at N-3 with clean inversion of configuration producing (R)-methyl 3-[1-(4-iodophenyl)ethyl]-3H-imidazole-4-carboxylate (4-iodo-MTO) IA. Finally, 4-iodo-metomidate is transformed to the 4-trimethylstannyl derivative IIA to serve as a precursor for labelling ETO and MTO with radiohalogen IB.

Compounds of formula II wherein L represents a leaving group, may be prepared by standard stannylation techniques. The exchange of X (iodine) for the trialkylstannyl substituent (L) is catalysed by tetrakis (triphenylphosphane) palladium to give a stannylated compound of formula IIA.

Radiohalogenated compounds of formula IB are conveniently prepared by reacting a compound of formula IIA with radiohalogen (Iodine-123; iodine-131) in the presence of an oxidizing agent, at room temperature.

The radioligand $^{131}$I-MTO is produced with a specific activity of 1 MBq/nmol, resp. 27.3 µCi/nmol.

The following Examples illustrate the preparation of compounds according to the invention.

The compounds in accordance with the present invention potently and selectively bind to adrenocortical membranes (cytochrome P-450 β-hydroxylase).

Radioligand Binding

Whole adrenals from adult male Wistar rats were homogenized in 10 mM $K_2HPO_4$/10 mM HEPES (pH 7.1) with a glass/teflon piston (Potter-type). The homogenate was centrifuged at 35.000×g for 10 min, the pellet was resuspended in fresh buffer and centrifuged again. Membranes were washed 2 more times and stored as aliquots at −80° C.

[$^{131}$I]MTO Binding Procedure

Glass vials containing 0.5 ml of 10 mM $K_2HPO_4$ 10 mM HEPES, 150 mM NaCl (pH 7.1), 20.000-40.000 cpm [$^{131}$I] MTO together with 2 nM 4-iodo-MTO as carrier (i.e. 1 pmol/vial, resulting in a specific activity of 9-18 Ci/mmol), and the adrenal membrane suspension corresponding to 0.2 mg tissue/vial, were immersed in a 23° C. water bath for 20-30 min. After incubation, membranes with bound radioligand were isolated by filtration through Whatman GF/B glass fiber filters (presoaked in buffer), followed by 2×4 mL washings with buffer, then filters were measured in a gamma-spectrometer.

The association time course of [$^{131}$I]MTO to rat adrenal membranes was evaluated at three ligand concentrations, namely 2 nM, 4 nM, and 11 nM of 4-iodo-MTO, respectively (data pooled from 7 experiments). Computerized curve fitting to the association function B(t)=$B_0$·[1+exp(−v.t)] resulted in observable association rate constants of v=0.65 min$^{-1}$, 1.23 min$^{-1}$, and 1.34 min$^{-1}$ corresponding to association half-times from 30 to 60 seconds.

For dissociation experiments, membranes were fully equilibrated with 2 nM radioligand, and the dissociation was initiated by the addition of excess unlabelled 4-iodo-MTO and stepwise filtration at 15 sec intervals. Four individual experiments demonstrated fast reversibility of binding and resulted in a dissociation constant of b=0.33±0.05 min$^{-1}$ and derived dissociation half-times from 1.8 to 2.4 min.

For saturation studies 2-100 nM 4-iodo-MTO carrier was used. See summary in FIG. 1. Saturation analysis of [$^{131}$I] MTO binding to rat adrenal membranes (4 representative experiments) produced 15 linear Eadie-Hofstee plots suggesting a single binding site. $K_D$=7.4±2.8 nM (15);

$B_{max}=2.4\pm0.4$ pmol/mg tissue (15). Incubation for 30 minutes using 10 mM $K_2HPO_4$/10 mM HEPES, 150 mM NaCl (pH 7.1). 0.2 mg tissue bind ~10% of the free ligand (0.1 pmol).

Displacement of [$^{131}$I]MTO Binding (FIG. 2)

Compounds of formula I and derivatives were evaluated as competitive inhibitors of [$^{131}$I]MTO binding. Test compounds were incubated at 0.01-100 nM concentrations. Non-specific binding was determined with etomidate (10 µM). The reaction was initiated by the addition of membrane and was terminated by filtration through Whatman GF/B filters (presoaked in buffer), followed by 2×4 mL washings with buffer. The filters containing membranes with bound radioligand were measured in a gamma-spectrometer.

$IC_{50}$ values (the molar concentration of compound necessary to inhibit binding by 50%) were determined for each test compound by non-linear, least squares regression analysis, using an iterative curve fitting routine.

The $IC_{50}$ values for binding to the cytochrome $P-450_{11\beta}$ enzyme system obtained for derivatives of etomidate resp. metomidate of the accompanying Examples were below 10 nM in each case. Moreover, it was demonstrated that (R)-configuration of the methyl substituent at the chiral C-atom is essential for binding, (S)-configuration is not tolerated ($IC_{50}$=492 nM); cleavage of the ester results in deactivation, the free acid (ETO-acid) is inactive ($IC_{50}$=123 µM); modification of the ester by 2-fluoroethyl (FETO) is tolerated without a loss of affinity ($IC_{50}$=3.0 nM); the ethyl ester (etomidate) shows the highest potency ($IC_{50}$=1.1 nM); the methyl ester (metomidate; $IC_{50}$=3.7 nM) and 4-iodo-MTO ($IC_{50}$=9.0 nM) show similar potencies. Metyrapone, a known, clinically used inhibitor, showed micromolar potency ($IC_{50}$=1.2 µM) when tested in this assay.

In Vivo Evaluation of $^{131}$I-MTO (FIGS. 3, 4)

Method: $^{131}$-MTO was used with a radiochemical purity >99% and a specific activity of 57 GBq/µmol. The radiotracer (0.51.1 MBq; 10-20 µCi) was injected into the tail vein of rats (female, 180-220 gram). Groups of four rats were sacrificed at specified times up to 24 hours post injection. The organs were excised and weighed, the radioactivity was measured at constant geometry using a gamma-spectrometer with a NaI(Tl)-crystal. The data were expressed as percent of injected dose (ID) per organ and as percent of ID per gram tissue.

Results: $^{131}$-MTO showed high specific uptake in the adrenals of approximately 10% ID/g tissue with a radioactivity plateau for 2 hours. The radiotracer is eliminated both by hepatobiliary and by renal excretion. Renal activity is attributed to $^{131}$I-ETO-acid, which results from enzymatic cleavage of the methyl ester. The renal activity is increasing up to 4 hours post injection. Based on calculations of the target-to-non-target-ratios the highest contrast for imaging of the adrenals is observed up to one hour post injection.

Thus, [$^{131}$I]-I-MTO shows a high potential as radiotracer for the functional imaging of adrenal pathology.

Similar distribution kinetics are demonstrated with $^{18}$F-fluoroetomidate. FIG. 5.

The present invention is described below in more detail in connection with the synthesis of the radiotracer (R)-3-[1-(4-[$^{131}$I]iodophenyl)ethyl]-3H-imidazole-4-carboxylic acid methyl ester ($^{131}$I-MTO); The example is given merely for illustrative purposes and shall in no way be understood as a limitation of the scope of the present invention which is given by the patent claims.

EXAMPLES

Example 1

Preparation of (R)-3-[1-(4-[$^{131}$I]iodophenyl)ethyl]-3H-imidazole-4-carboxylic acid methyl ester i.e. ($^{131}$I-MTO)

a. Preparation of (S)-1-(4-iodophenyl)ethanol (III)

The substituted (S)-alcohol was prepared according to scheme 1

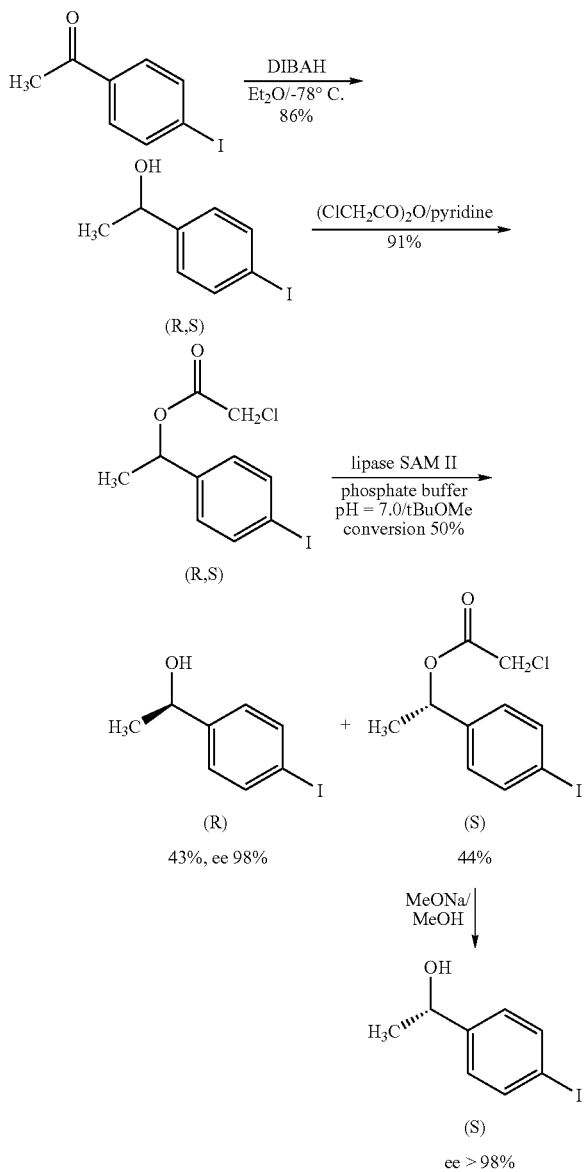

Preparation of (±)-1-(4-Iodophenyl)ethanol

A solution of DIBAH (16.45 cm³, 24.67 mmol, 1.5 M solution in toluene) was added dropwise to a stirred mixture of 4-iodoacetophenone (5.08 g, 20.65 mmol) in dry diethyl ether (50 cm³) at −78° C. in an atmosphere of argon. After stirring for 2 h at −78° C., methanol (2 cm³) was added and stirring was continued for 30 min at room temperature before water (10 cm³) was added cautiously. 30 min later, the aluminum hydroxide formed was dissolved in hydrochloric acid (50 cm³, 2 M) under cooling with ice. The organic phase was separated, washed with water and a saturated aqueous solution of sodium hydrogen carbonate, dried (magnesium sulphate) and concentrated under reduced pressure. The crude product was purified by flash chromatography (hexane-dichloromethane 1:2; $R_f$=0.20) on silica gel and bulb to bulb distillation (0.2 mmHg/90-95° C.) to give (±)-(3.91 g, 86%) as liquid which crystallised; mp 47-49° C. (lit. 50.5-51.5° C.).

$\delta_H$ (400.13 MHz, CDCl₃) 1.40 (3 H, d, J 6.5, CH₃CH), 1.75 (1 H, br s, OH), 4.78 (1 H, q, J 6.5, CH₃CH), 7.06 (2 H, d, J 8.5, 2×H$_{arom}$), 7.60 (2 H, d, J 8.5, 2×H$_{arom}$); $\delta_c$(100.61 MHz, CDCl₃) 25.62 (CH₃CH), 70.25 (CH₃CH), 93.09 (IC$_{arom}$), 127.79 (2 C, 2×HC$_{arom}$), 137.94 (2 C, 2×HC$_{arom}$), 145.86 (C$_{arom}$).

Preparation of (±)-1-(4-Iodophenyl)ethyl chloroacetate

Dry pyridine (6.0 cm³) and chloroacetic anhydride (6.2 g, 36.26 mmol) were added to a stirred solution of (±)-1-(4-Iodophenyl)ethanol (5.95 g, 24.0 mmol) in dry dichloromethane (100 cm³) at 0° C. under an atmosphere of argon. When the reaction was finished (2 h, TLC: hexane-dichloromethane 3:2, Rf=0.35 for ester), water (40 cm³) and concentrated hydrochloric acid (3.6 cm³) were added. After stirring for 10 min, the organic phase was separated and the aqueous phase was extracted with dichloromethane (3×15 cm³). The combined organic phases were washed with water (50 cm³) and a saturated solution of sodium hydrogen carbonate (25 cm³), dried (sodium sulfate) and evaporated under reduced pressure. The residue was purified by flash chromatography (hexane-dichloromethane 3:2, Rf=0.35) on silica gel and bulb to bulb distillation (0.1 mmHg/105° C.) to give chloroacetate (7.09 g, 91%) as a colourless liquid (Found: C, 36.9; H, 3.25, C₁₀H₁₀ClIO₂ requires C, 37.0; H, 3.1%), which crystallised spontaneously; mp 50-51° C. ν$_{max}$ (Si, film)/cm⁻¹ 2983, 1756, 1591, 1488, 1285, 1176, 1063, 1007; δH (400.13 MHz, CDCl₃) 1.54 (3 H, d, J 7.0, CH₃CH), 4.03 (2 H, d, J 14.8, CH₂Cl), 5.90 (1 H, q, J 7.0, CH₃CH), 7.08 (2 H, d, J 8.5, 2×H$_{arom}$), 7.68 (2 H, d, J 8.0, 2×H$_{arom}$); $\delta_c$ (100.61 MHz, CDCl₃); 21.84 (CH₃CH), 40.99 (CH₂Cl), 73.84 (CH₃CH), 93.85 (IC$_{arom}$), 128.08 (2 C, 2×HC$_{arom}$), 137.75 (2 C, 2×HC$_{arom}$), 140.30 (C$_{arom}$), 166.45 (CO).

b. Enzymatic Hydrolysis of (±)-1-(4-iodophenyl)ethyl chloroacetate

Racemic chloroacetate (0.835 g, 2.57 mmol) t-butyl methyl ether (4 cm³) and phosphate buffer (50 mmol, sterile, 17 cm³) and lipase SAM 11 (96 mg) were stirred vigorously at room temperature. The pH was kept constant at 7.0 by addition of 0.5 N sodium hydroxide using an autotitrator.

98% of the calculated amount of base were consumed in 2.6 hr. The reaction was stopped after another 14 h (virtually no base was consumed during the last 9 hr) by bringing the pH to about 2.0 using 2 N hydrochloric acid. Water (100 cm³) was added and ester and alcohol were extracted with dichloromethane (3×200 cm³). The combined organic layers were washed with water and a saturated solution of sodium hydrogen carbonate (50 cm³ each), dried (sodium sulfate), and evaporated under reduced pressure to leave a residue which was purified by flash chromatography (hexane-dichloromethane 3:2 for chloroacetate, Rf=0.35; hexane-dichloromethane 1:2 for alcohol, Rf=0.20) on silica gel to give (S)-chloroacetate (0.367 g, 44%, [α]²⁰D=82.57 (c 2.57 in acetone), ee 98% and [α]²⁰D=+35.68 (c 2.04 in acetone) after chemical hydrolysis) as a liquid and (R)-alcohol (0.393 g, 43%, ee 98%; [α]²⁰D=+35.92 (c 1.96 in acetone) before crystallisation from petroleum ether (40-60° C.)-dichloromethane, afterwards [α]²⁰D=+35.95 (c 2.05 in acetone); mp 48-49° C.) as a crystalline solid.

Chemical Hydrolysis of (S)-(1-(4-iodophenyl)ethyl chloroacetate (S)-Chlorocetate (0.340 g, 1.05 mmol) was dissolved in methanol/sodium methoxide (17 cm³, obtained by dissolving 69 mg of sodium in 30 cm³ of dry methanol). After 1 hr, water (few drops) was added and solution was concentrated under reduced pressure. Water (30 cm³) and dichloromethane (15 cm³) were added. The organic layer was separated and the aqueous one was extracted with dichloromethane (2×15 cm³). The combined organic layers were dried (sodium sulfate) and evaporated to leave a residue, which was purified by flash chromatography (hexane-dichloromethane 1:2, Rf=017) to give (S)-alcohol (0.240 g, 92%, ee 98%) as a crystalline solid.

c. (R)-(+)-Methyl 3-[1-(4-Iodophenyl)ethyl]-3H-imidazole-4-carboxylate

A solution of (S)-alcohol (1.98 g, 7.98 mmol, ee>98%) in dry THF (14.5 cm³) was added dropwise to a stirred solution of methyl 3H-imidazole-4-carboxylate (1.008 g, 7.98 mmol) and triphenylphosphane (2.503 g, 9.43 mmol) in dry THF (22.0 cm³) in an atmosphere of argon −30° C. Then, a solution of di-t-butyl azodicarboxylate (2.204 g, 9.57 mmol) in dry THF (14.5 cm³) were added and the stirred reaction mixture was allowed to warm up from −30° C. to 0° C. within 2.5 hr. No alcohol could by detected by TLC (diethyl ether-diisopropylamine 10:1). The reaction mixture was concentrated under reduced pressure. The residue was mixed with diethyl ether (36 cm³) and stirred for 2 h. The crystals (triphenylphosphanoxide and hydrazo ester) were collected and washed with diethyl ether (3×15 cm³). The filtrate was evaporated und reduced pressure to leave a residue, which was purified by flash chromatography (hexanes-diethyl ether-diisopropylamine 50:30:1; TLC: diethyl ether-diisopropylamine 10:1, Rf=0.44 for iodide, 0.54 for metomidate) on silica gel to give p-iodometomidate (1.91 g, 67%, ee 99%); [a]²⁰D+76.0 (c 1.09 in acetone).

Found: C. 43.8; H.3.7; N, 7.9. C₁₃H₁₃IN₂O₂ requires C, 43.7; H, 3.8; N, 7.7, ν$_{max}$ (Si, film)/cm⁻¹ 2981, 2947, 1712, 1487, 1437, 1363, 1220, 1134, 1111, 1006; δ$_H$(400.13 MHz, CDCl₃) 1.81 (3 H, d, J 7.5, CH₃CH), 3.77 (3 H, s, OCH₃), 6.26 (1 H, q, J 7.5, CH₃CH), 6.88 (2 H, d, J 8.5, 2×H$_{arom}$), 7.63 (2 H, d, J 8.5, 2×H$_{arom}$), 7.73 (1H, s, H$_{hetarom}$), 7.75 (1H, d, J 1.0, H$_{hetarom}$); $\delta_c$ (100.61 MHz, CDCl₃) 22.09 (CH₃CH), 51.47 (OCH₃), 54.96 (CH₃CH), 93.46 (IC$_{arom}$), 122.29 (2 C, 2×HC$_{arom}$), 128.02 (2 C, 2×HC$_{arom}$), 137.94 (C$_{arom}$), 138.40 (HC$_{hetarom}$), 139.54 (HC$_{hetarom}$), 141.10 (CCO), 160.58 (CO).

d. (R)-(+)-Methyl 3-[1-(4-trimethylstannylphenyl) ethyl]-3H-imidazole-4-carboxylate Hexamethylditin (0.645 g. 3.2 mmol, 6.5 cm³ of a solution of 1.0 g hexamethylditin in 10 cm³ of dry toluene), tetrakis (triphenylphosphane)palladium (58 mg, 5 mol %) and triethylamine (1.6 cm³, 11.6 mmol) were added to a stirred solution of iodometomidate (0.368 g. 1.03 mmol, ee >98%) in an atmosphere of argon and refluxed (bath temperature 135° C.) for 17 hr. The cooled solution was concentrated under reduced pressure and the residue was purified by flash chromatography (hexane-diethyl ether-diisopropylamine 60:30:1; TLC:diethyl ether-diisopropylamine 10:1, R$_f$=0.71 for stannane, R$_f$=0.50 for iodometomidate) on silica gel to give stannane (0.377 g, 96%) as a crystalline solid (Found: C, 48.7; H, 5.6 N, 7.1, $C_{16}H_{22}N_2O_2Sn$ requires C, 48.9; H, 5.6; N, 7.1%); mp 77-79° C. (from hexane); $[a]^{20}D=+82.09$ (c 2.06 in acetone).

$v_{max}$ (Si, film)/cm$^{-1}$ 2981, 1715, 1437, 1362, 1218, 1133, 1110, 1049; $\delta_H$ (400.13 MHz, CDCl$_3$) 0.25 (9 H, s, (CH$_3$)$_3$Sn, $^{117/119}$Sn satellites, 2×d, J 53.2 and 55.2), 1.82 (3 H, d, J 7.0, CH$_3$CH), 3.77 (3 H, s, OCH$_3$), 6.30 (1 H, q, J 7.0, CH$_3$CH), 7.13 (2 H, d, J 8.0, 2×H$_{arom}$, $^{117/119}$Sn satellites, d, J 9.0), 7.43 (2 H, d, J 8.0, 2×H$_{arom}$, $^{117/119}$Sn satellites, d, J 42.7), 7.71 (1 H, s, H$_{hetarom}$), 7.74 (1 H s, H$_{hetarom}$); $\delta_c$ (100.61 MHz, CDCl$_3$) −9.61 (3 C, (CH$_3$)$_3$Sn), 22.16 (CH$_3$CH), 51.40 (OCH$_3$), 55.30 (CH$_3$CH), 122.31 (C$_{arom}$), 125.81 (2×C, 2×HC$_{arom}$), $^{117/119}$Sn satellites, d, J 45.9), 136.28 (2×C, 2×HC$_{arom}$, $^{117/119}$Sn satellites, d, J 36.8), 122.29 (2 C, 2×HC$_{arom}$), 128.02 (2 C, 2×HC$_{arom}$), 137.94 (C$_{arom}$), 138.23 (HC$_{hetarom}$), 139.84 (HC$_{hetarom}$), 141.00 (C$_{arom}$ or CCO), 142.24 (CCO or C$_{arom}$), 160.68 (CO).

e. Preparation of (R)-(+)-Methyl 3-[1-(4-[$^{131}$I]Iodophenyl)ethyl]-3H-imidazole-4-carboxylate 30 µg 4-Stannan-MTO is reacted with [$^{131}$I]iodide in 10-20 µl NaOH (0.05N), 15 µl chloramine-T (1 mg/ml, aqueous), 6 µl hydrochloric acid (1 N) during 1 min at ambient temperature. The reaction is stopped with 6 µl NaOH (1 N), to give the 'compound with a radiochemical yield: >95%, radiochemical purity: >99%, specific activity: 1 MBq/nmol; chemical purity: >95%.

By following the preparation as described above for (R)-methyl 3-[1-(4-iodophenyl)ethyl]-3H-imidazole-4-carboxylate (4-iodo-MTO) further compounds according to the invention can be synthesized, such as e.g. (R)-ethyl 3-[1-(4-iodophenyl)ethyl]-3H-imidazole-4-carboxylate (4-iodo-ETO) and their radioactive analogues.

Literature Related to the Prior Art

Basmadjian G P, Hetzel K R, Ice R D, Beierwaltes W H (1975) Synthesis of a new adrenal cortex imaging agent 6□-[$^{131}$I]-iodomethyl-19-norcholest-5(10)en-3□-ol (NP-59). J. Labelled Compd. & Radiopharm. XI: 427-434.

Sakar S D, Ice R D, Beierwaltes W H, Gill S P, Balanchandran S, Basmadjian G P (1976) Selenium-75-19-selenocholesterol—a new adrenal scanning agent with high concentration in the adrenal cortex. J Nucl Med 17: 212-217.

W. H. Beierwaltes, D. M. Wieland, R. D. Ice, J. E. Seabold, S. D. Sarkar, S. P. Gill, and S. T. Mosley: Localization of radiolabeled enzyme inhibitors in the adrenal gland. J. Nucl. Med., 17(11), 998-1002, 1976.

W. H. Beierwaltes, D. M. Wieland, S. T. Mosley, D. P. Swanson, S. D. Sarkar, J. E. Freitas, J. H Thrall, and K. R. Herwig: Imaging the adrenal glands with radiolabeled inhibitors of enzymes: concise communication. J. Nucl. Med., 19(2), 200-203, 1978.

Wu J. L., Wieland D. M., Beierwaltes W. H., Swanson D. P., Brown L. E.: Radiolabelled enzyme inhibitors—enhanced localization following enantiomeric purification. J. Labelled Compd. & Radiopharm., XVI(1), 6-9, 1979.

Wieland D M: Radiolabeled enzyme inhibitors—Adrenocortical enzymes. In: Receptor-binding radiotracers, Vol. I, 127-146, Ed. W. C. Eckelman, Chemical Rubber Co. Press, Cleveland, Ohio, 1982.

Robien W. and Zolle I. (1983) Synthesis of radioiodinated metyrapone—A potential agent for functional imaging of the adrenal cortex. Int. J. Appl. Radiat. Isot. 34: 907-914.

Allolio B, Stuttmann R, Fischer H, Leonhard W, Winkelman W (1983) Long-term etomidate and adrenocortical suppression. The Lancet ii, 626.

Zolle, W. Woloszczuk, and R. Höfer: Synthesis and in vitro evaluation of metyrapone derivatives as potential inhibitors of 11□-hydroxylase activity. In: Radiopharmaceuticals and labelled compounds, 337-342, IAEA-CN-45/67, Vienna, 1985.

Vanden Bossche H, Willemsens G, Cools W, Bellens D (1984) Effects of etomidate on steroid biosynthesis in subcellular fractions of bovine adrenals. Biochemical Pharmacology: 33(23), 3861-3868.

Engelhardt D (1994) Steroid biosynthesis inhibitors in Cushing's syndrome. Clin Investig 72: 481-488.

Weber M M, Lang J. Abedinpour F, Zeilberger K, Adelmann B, Engelhardt D (1993) Different inhibitory effect of etomidate and ketoconazole on the human adrenal steroid biosynthesis. Clin. Invest. 71: 933-938.

Yu, J., Zolle, I., Mertens, J., and Rakias, F.: Synthesis of 2-[$^{131}$I]-iodophenyl-metyrapone using Cu(I)-assisted nucleophilic exchange labelling: Study of the reaction conditions. Nucl. Med. & Biol. 22(2): 257-262 (1995).

Godefroi, E. F., Janssen, P. A. J., Van der Eycken, C. A. M., Van Heertum, A. H. M. T., Niemegeers, C. J. E. (1965) DL-1-(1-Arylalkyl)imidazole-5-caroxylate esters. A novel type of hypnotic agents. J. Med. Chem. 8: 220-223. Synthesis of etomidate U.S. Pat. No. 3,354,173 issued Nov. 21, 1967. Expired November 1984.

Reviews:

Mitsunobu O. (1981) Synthesis: 1-28.

Hughes D. L. (1992) Org. Reactions 42: 335-656.

Hughes D. L. (1996) Org. Prep. Proced. Int. 28: 127-164.

Reference for Iodinations:

Merkushev E. B. (1988) Synthesis: 923-937.

Reference for Radioiodinations:

Ali H. and van Lier J. E. (1996) Synthesis: 423-445. Baldwin

Literature for Enzymatic Hydrolysis:

Laumen K. and Schneider M. P. (1988) J. Chem. Soc. Chem. Comm.: 598-800.

References for Coupling with Mitsunobu:

Botta M., Summa V., Trapassi G., Monteagudo E., Corelli F. (1994) Tetrahedron: Asymmetry 5: 181-184.

Corelli F., Summa V., Brogi A., Monteagudo E., Botta M. (1995) J. Org. Chem. 60: 2008-2015.

Ref. for Destannylation

Baldwin R. M., Zea-Ponce Y., Zoghbi S. S., Laruelle M., Al-Tikriti M. S., Sybirska E. H., Malison R. T., Neumeyer J. L., Milius R. A., Wang S., Stabin M., Smith E. O., Charney D. S., Hoffer P. B., and Innis R. B., (1993) Evaluation of the monoamine uptake site ligand [$^{123}$I] methyl-3□-(4-iodophenyl)tropane-2□-carboxylate ([$^{123}$I]□-CIT) in non-human primates: pharmacokinetics, biodistribution and SPECT brain imaging coregistered with MRI. Nucl. Med. Biol. 20: 597-606.

Literature on Incidentalomas

Siren J E, Haapiainen R K, Huikuri K T, et al. (1993) Incidentalomas of the adrenal gland: 36 operated patients and review of literature. World J. Surg. 17: 634-639.

Reincke M, Fassnacht M, Vath S, Mora P, Allolio B (1996) Adrenal incidentalomas: A manifestation of the metabolic syndrome. Endocrine Research 22(4): 757-761.

Abecasis M, McLoughlin M J, Lange B, Kudlaw J E (1985) Serendipitous adrenal masses: Prevalence, significance and management. Am. J. Surg. 149: 783.

Herrera M F, Grant C S, van Heerden J A, et al. (1991) Incidentally discovered adrenal tumors: an institutional perspective. Surgery 110: 1014-1021.

Kloos R T, Gross M D, Francis I R, Korobkin M, Shapiro B (1995) Incidentally discovered adrenal masses. Endocrin Rev. 16: 460-484.

Literature Related to Toxic Effect of Etomidate When Used as a Hypnotic

Drake W M, Perry L A, Hinds C J, Lowe D G, Reznek R H, Besser G M (1998) Emergency and prolonged use of intravenous etomidate to control hypercortisolemia in a patient with Cushing's syndrome and peritonitis. J. Clin. Endocrinol. Metab. 83: 3542-3544.

Ledingham I, Watt I (1983) Influence of sedation on mortality in critically ill multiple trauma patients. Lancet, Jun. 4, 1270.

Lit. for 4-Fluoro-etomidate

De Coster R., Degryse A.-D., Van Dijk P., Ooms L. A. A., Lagerweij E. (1987) Comparison of the effects of etomidate and its fluoro analogue, R 8110, on plasma cortisol, 11□-deoxycortisol, 17□-hydroxyprogesterone and testosterone concentrations in dogs. J. vet. Pharmacol. Therap. 10: 227-232.

What is claimed is:

1. A radiohalogen-labelled compound of formula (I)

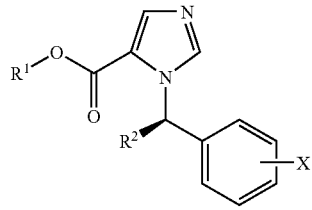

(I)

wherein $R^1$ is a linear or branched $C_1$-$C_4$ alkyl, and is optionally substituted with a halogen selected from the group consisting of F, Cl, Br, I;

$R^2$ denotes an alkyl group containing 1 or 2 carbon atoms; and

X is a radioactive halogen selected from the group consisting of $^{18}F$, $^{76}Br$, $^{82}Br$, $^{123}I$, $^{124}I$, $^{131}I$.

2. The radiohalogen-labelled compound of claim 1 having the formula (IA)

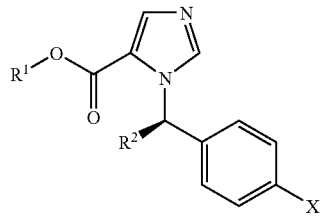

(IA)

wherein $R^1$, $R^2$, and X are as defined above.

3. The radiohalogen-labelled compound of claim 2, wherein X is radioactive iodine.

4. The radiohalogen-labelled compound of claim 1, wherein $R^1$ and $R^2$ are each methyl and X is $^{123}I$, and wherein the compound is $^{123}I$-metomidate ($^{123}I$-MTO).

5. The radiohalogen-labelled compound of claim 1, wherein $R^1$ is ethyl and $R^2$ is methyl and X is $^{131}I$, wherein the compound is $^{131}I$-etomidate ($^{131}I$-ETO).

* * * * *